(12) United States Patent
Shojaei et al.

(10) Patent No.: US 9,283,570 B2
(45) Date of Patent: Mar. 15, 2016

(54) NANOPARTICLE SEPARATION METHODS AND COMPOSITIONS

(75) Inventors: Borzoyeh Shojaei, Folsom, CA (US); George Hanki Chan, Cupertino, CA (US)

(73) Assignee: SICPA HOLDING SA (CH)

(*) Notice: Subject to any disclaimer, the term of this patent is extended or adjusted under 35 U.S.C. 154(b) by 841 days.

(21) Appl. No.: 13/115,777

(22) Filed: May 25, 2011

(65) Prior Publication Data

US 2012/0132570 A1    May 31, 2012

Related U.S. Application Data

(60) Provisional application No. 61/348,053, filed on May 25, 2010.

(51) Int. Cl.
| | |
|---|---|
| *B03B 5/00* | (2006.01) |
| *B03B 13/00* | (2006.01) |
| *B03B 1/00* | (2006.01) |
| *B03B 5/30* | (2006.01) |
| *B03B 5/32* | (2006.01) |
| *B03B 5/44* | (2006.01) |
| *B82Y 30/00* | (2011.01) |

(Continued)

(52) U.S. Cl.
CPC ............... *B03B 13/005* (2013.01); *B03B 1/00* (2013.01); *B03B 5/30* (2013.01); *B03B 5/32* (2013.01); *B03B 5/44* (2013.01); *B82Y 30/00* (2013.01); *B82Y 40/00* (2013.01); *G01N 21/658* (2013.01)

(58) Field of Classification Search
CPC .............. B03B 1/00; B03B 5/30; B03B 5/32; B03B 5/44; B03B 13/005; B82Y 30/00; B82Y 40/00

USPC ............. 209/155, 172.5, 173, 195, 198, 199, 209/203–205; 252/582; 977/777, 900, 902
See application file for complete search history.

(56) References Cited

U.S. PATENT DOCUMENTS

| | | | |
|---|---|---|---|
| 5,096,066 A | * | 3/1992 | Kindig ........................ 209/172.5 |
| 6,514,767 B1 | | 2/2003 | Natan |

(Continued)

OTHER PUBLICATIONS

Akthakul, et al., "Size Fractionation of Metal Nanoparticles by Membrane Filtration", Adv. Mater., 2005, Vo. 17, No. 5, pp. 532-535.

(Continued)

*Primary Examiner* — Joseph C Rodriguez
*Assistant Examiner* — Kalyanavenkateshware Kumar
(74) *Attorney, Agent, or Firm* — Swanson & Bratschun, L.L.C.

(57) ABSTRACT

Methods of separating one type of nanoparticle from another type of nanoparticle in a mixture including more than one type of nanoparticle are disclosed. The methods may include suspending a mixture of the various types of nanoparticles in a liquid and modifying a characteristic of the liquid. Thereafter, a force may be applied to the nanoparticles within the mixture causing one type of nanoparticles to separate from another type of nanoparticles. The applied force may be the force of gravity, or it may be an induced force such as a centrifugal force applied with a centrifuge or similar apparatus. Upon the occurrence physical separation, sub-populations of nanoparticles may be removed from the suspension or segregated. Alternatively the methods may include modifying a type of nanoparticle in suspension. Alternative embodiments include nanoparticles modified in suspension to provide for separation from other types of nanoparticles.

6 Claims, 14 Drawing Sheets

(51) Int. Cl.
*B82Y 40/00* (2011.01)
*G01N 21/65* (2006.01)

(56) References Cited

U.S. PATENT DOCUMENTS

| | | | |
|---|---|---|---|
| 7,192,778 B2 | 3/2007 | Natan | |
| 7,443,489 B2 | 10/2008 | Natan | |
| 7,452,726 B2 * | 11/2008 | Chou et al. | 436/63 |
| 2004/0224380 A1 * | 11/2004 | Chou et al. | 435/29 |
| 2006/0054506 A1 | 3/2006 | Natan et al. | |
| 2010/0084320 A1 * | 4/2010 | Mason | 209/155 |

OTHER PUBLICATIONS

Bai, et al., "Rapid Separation and Purification of Nanoparticles in Organic Density Gradients", J. Am. Chem. Soc., 2009, pp. A-E.

Chen, et al., "Measuring Ensemble-Averaged Surface-Enhanced Raman Scattering in the Hotspots of Colloidal Nanoparticle Dimers and Trimers", 2009, J. Am. Chem. Soc., pp. A-B.

Chen, et al., "High-Purity Separation of Gold Nanoparticle Dimers and Trimers", 2009, J. Am. Chem. Soc., pp. A-B.

Freeman, et al., "Size Selection of Colloidal Gold Aggregates by Filtration: Effect on Surface-enhanced Raman Scattering Intensities", J. Raman Spectroscopy, 1999, 30, pp. 733-738.

Goddard, et al., "High-Resolution Spectral Analysis of Individual Sers-Active Nanoparticles in Flow", J. Am. Chem. Soc., 2009, pp. A-J.

Hwang, et al., "Separation of Nanoparticles in Different Size and Compositions by Capillary Electrophoresis", Bull. Korean Chem. Soc., 2003, vol. 24, No. 5, pp. 684-686.

Roca, et al., "Linear Assembly of Gold Nanoparticle Clusters via Centrifugation", Langmuir, 2009, pp. A-G & Supporting Info.

Sweeney, et al., "Rapid Purification and Size Separation of Gold Nanoparticles via Diafiltration", 2005, J. Am. Chem. Soc., pp. A-H.

Trefry, et al., "Size Selection and Concentration of Silver Nanoparticles by Tangential Flow Ultrafiltration for Sers-Based Biosensors", 2010, J. Am. Chem.Soc., pp. A-C.

Zhu, et al., "Size Differentiation and Absolute Qualification of Gold Nanoparticles via Single Particle Detection with a Laboratory-Built High-Sensitivity Flow Cytometer", J. Am. Chem. Soc., 2010, pp. A-C.

* cited by examiner

NANOPARTICLE SEPARATION METHODS AND COMPOSITIONS

RELATED APPLICATIONS

This application claims priority from U.S. Provisional Patent Application Ser. No. 61/348,053, filed Mar. 25, 2010 entitled "Nanoparticle Separation Methods and Compositions," which is hereby incorporated by reference.

STATEMENT OF RIGHTS TO INVENTIONS MADE UNDER FEDERALLY SPONSORED RESEARCH

This work was supported by the United States government, in part, by grant(s) from the United States Department of Defense, (DARPA Grant No(s). FA9550-O8-1-0221). Thus, the United States government has certain rights to this invention.

BACKGROUND

SERS nanotags and other optically detectable nanoparticles have proved useful for marking objects for identification and tracking. SERS nanotags are nanoparticulate optical detection tags which function through surface enhanced Raman scattering (SERS). SERS is a laser-based optical spectroscopy that, for molecules or other materials, generates a fingerprint-like vibrational spectrum with features that are much narrower than typical fluorescence. SERS nanotags and other types of optical detection nanotags can be fabricated in various sizes, shapes and with some control over selected configuration elements. For example, a quantity of nanotags may be fabricated generally having a metal nanoparticle core and semiconductor shell. Within the total quantity of particles fabricated, some examples might have a single particle core and others a double particle core or a multiple particle core. Some individual configurations of generally related particle types have been observed to have enhanced performance characteristics. For example a SERs nanotag with two or more cores is typically observed to be spectroscopically brighter than a single core particle fabricated from the same materials or in the same batch. It would thus be desirable, for example, to sort the multiple core particles from the single core particles in a given batch.

In addition, it is exceptionally difficult or impossible to fabricate completely homogeneous populations of a selected particle configuration. For example, if SERS nanotags with two cores and a single shell are desired, fabrication parameters can be controlled to favor the creation of the desired configuration, but all known fabrication techniques will produce substantial quantities of tags with single cores as well. Thus, sorting becomes desirable, but it is exceptionally difficult to sort nanoparticles using conventional filtering techniques because of the nanoscale particle size.

In particular, known separation techniques such as filtering, centrifuging, or more advanced separation techniques are often difficult or impossible to implement with suspensions of nanoparticles. Known separation techniques can be particularly difficult to implement when the suspension contains more than one distinguishable nanoparticle type, size, shape or composition and it is desired to separate the different types of nanoparticles from each other. The embodiments disclosed herein are directed toward overcoming one or more of the problems noted above.

SUMMARY OF THE EMBODIMENTS

One embodiment is a method of separating one type of nanoparticle from another type of nanoparticle in a mixture including more than one type of nanoparticle. As used herein a "type" of nanoparticle is a nanoparticle of any size, shape, mass, composition, or having surface or internal characteristics which are different from another type of nanoparticle. The method may include suspending a mixture of the various types of nanoparticles in a liquid and modifying a characteristic of the liquid. Thereafter, a force may be applied to the nanoparticles within the mixture causing one type of nanoparticles to separate from another type of nanoparticles. The applied force may be the force of gravity, or it may be an induced force such as a centrifugal force applied with a centrifuge or similar apparatus. Upon the occurrence physical separation, sub-populations of nanoparticles may be removed from the suspension or segregated.

The embodiment described above includes modifying a characteristic of a suspension liquid. Any suitable liquid may be used to suspend and provide for separation of the selected nanoparticles. The characteristic of the liquid which is modified may include, but is not limited to, the liquid temperature, liquid pressurization, liquid viscosity or liquid composition.

An alternative method of separating nanoparticles by type from a mixture of multiple types of nanoparticles comprises suspending the mixture of nanoparticles in liquid and modifying one or more characteristics of a selected type of nanoparticle. Thereafter, a force may be applied to the mixture and separation may proceed as described above. The characteristic of the nanoparticle which is modified may include but is not limited to one or more of nanoparticle interaction potential, nanoparticle surface geometry, nanoparticle shape, nanoparticle size, nanoparticle effective radius, nanoparticle concentration, nanoparticle surface composition or other nanoparticle surface characteristics.

An alternative embodiment is a nanoparticle modified in a liquid suspension to provide for the separation of a collection of the modified nanoparticles from nanoparticles of a different type. The modification of the selected nanoparticle may include but is not limited to modification of nanoparticle interaction potential, nanoparticle surface geometry, nanoparticle shape, nanoparticle size, nanoparticle effective radius, nanoparticle concentration, nanoparticle surface composition or other nanoparticle surface characteristics.

BRIEF DESCRIPTION OF THE DRAWINGS

FIG. 8a is an SEM image of a portion of the mixture of nanoparticle types of FIG. 2a remaining after a fourth separation step and the removal of the nanoparticles of FIG. 7a.

DETAILED DESCRIPTION

Figure 1:
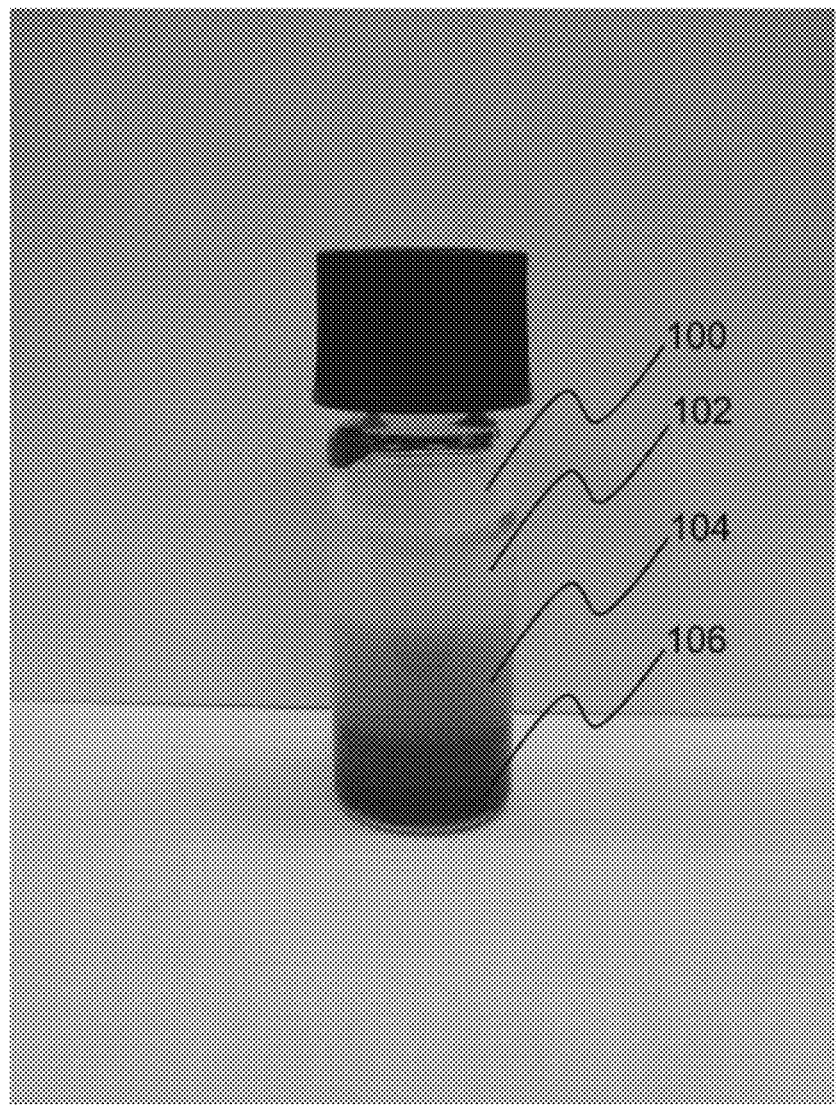
FIG. 1 is a photograph of a partially separated suspension of various types of nanoparticles.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The embodiments disclosed herein relate to methods and apparatus for separating mixtures of any type of distinguishable nanoparticles. The examples discussed below relate to particles that are spectroscopically active although the disclosed methods are not limited to spectroscopically active particles. In particular, the techniques may be implemented to separate particles which are surface-enhanced spectroscopy (SES) active. Representative SES techniques include but are not limited to SERS, SERRS and others. Surface enhancement in various other spectroscopy methods or systems has been observed. The most widely studied have been surface-enhanced Raman scattering and surface-enhanced fluorescence (SEF). But a variety of other surface enhanced phenomena have been observed including surface-enhanced hyper Raman scattering (SEHRS), surface-enhanced hyper Raman resonance scattering (SEHRRS), surface-enhanced Rayleigh scattering, surface-enhanced second harmonic generation (SHG), surface-enhanced infrared absorption reflectance (SEIRA), and surface-enhanced laser desorption ionization (SELDI). These are part of a wider field known as plasmon enhancement or plasmon-enhanced spectroscopy, which in addition to the phenomena mentioned above includes surface plasmon enhanced emission (such as SPASERS—surface plasmon amplification of spontaneous emission of radiation), plasmon enhanced diffraction, and plasmon enhanced optical transmission. Plasmon enhancement is also a method to increase the efficiency of solar cells.

The methods disclosed herein are well suited to separate particles that are intended for use as a taggant. For example, a quantity of SERS nanotags might be prepared that has sub-populations of particles with single cores, a double cores and multiple core. These variations are alternatively referred to as aggregated and unaggregated particles herein. The single core particles are typically observed to return a less spectroscopically bright signal upon interrogation, therefore for taggant purposes it is desirable to select for double or multiple core particles. The described separation techniques thus provide for the selection of the best particles for a given purpose while the balance of the un-selected particles may be recycled thus conserving material and reducing cost.

In general, taggants are materials, substances, molecules, ions, polymers, nanoparticles, microparticles, or other matter, incorporated into, onto or otherwise associated with objects for the purposes of identification or quantitation. More specifically, taggants are used in activities and products including but not limited to detection, analysis, and/or quantification measurements related to brand security, brand protection, trademark protection, product security, product identification, brand diversion, bar-coding, grey market remediation, friend-or-foe analysis, product life cycle analysis, counterfeiting, anti-counterfeiting, forensic analysis of authenticity, authentication, biometrics, object tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, and standoff detection/identification.

Taggants can be added to all forms of matter, including but not limited to solids, liquids, gases, gels, foams, semi-solids, glasses, plasmas, liquid crystals, amorphous and magnetically-ordered solids, superconductors, superfluids, Bose-Einstein condensates, and supersolids.

A typical taggant prepared and separated according to the disclosed methods might be a SERS nanotag which includes a metal nanoparticle core and a $SiO_2$ (glass) or other silicon containing encapsulant. Other materials including but not limited to various types of polymers may also be used as an encapsulant or shell. Details concerning the use, manufacture and characteristics of a typical SERS nanotag are included in U.S. Pat. No. 6,514,767, entitled "Surface Enhanced Spectroscopy-Active Composite Nanoparticles;" U.S. Pat. No. 7,192,778, entitled "Surface Enhanced Spectroscopy-Active Composite Nanoparticles;" U.S. Pat. No. 7,443,489, entitled "Surface Enhanced Spectroscopy-Active Composite Nanoparticles;" and U.S. Published Patent Application No. US 2006-0054506, entitled "Surface Enhanced Spectrometry-Active Composite Nanoparticles;" each of which patents and publications is incorporated herein by reference for all matters disclosed therein.

Nanoparticles suspended in a liquid exhibit Langevin dynamics. Accordingly, the motion of a nanoparticle in a suspension is a function of the suspension liquid temperature, the liquid viscosity, nanoparticle geometry, nanoparticle mass, and nanoparticle interaction potential. Nanoparticles which are different in structure and/or composition will exhibit different dynamics in a liquid suspension. The embodiments disclosed herein describe processes and characteristics or functional attributes of certain nanoparticles which provide for the efficient separation of structurally or compositionally differing nanoparticles that are in liquid suspension and under a force.

In general, nanoparticles of different geometries and/or compositions are separated by controlling properties of the suspension to maximize the difference between the diffusivities and average velocities of different particles. The diffusivity and average velocities of the various nanoparticles are adjusted by implementing control over one or any combination of the following suspension properties: (1) temperature of the suspension, (2) viscosity of the liquid, (3) nanoparticle interaction potential, and (4) effective radius or surface geometry of the nanoparticle.

The specific particles and methods described in detail herein are representative examples described for the purpose of illustrating the general embodiments of the invention. The specifically described examples are not intended to limit the scope of this disclosure. For example, the methods described herein are relevant to many types of particles not described with particularity.

Certain methods described herein may be generally understood by considering a mixture of an equivalent number of two nanoparticle types, one with greater size or mass than the other. The two types of particles may be, at a given point in time, uniformly distributed in a liquid suspension. Uniform distribution would be expected for example immediately after the mixture was prepared and mixed. A force, for example gravity, immediately begins acting upon the suspension, and therefore, the particles will tend toward a motion in the direction of the applied force. At room temperature, both particle types may settle within the suspension, with little difference between the respective sedimentation velocities.

However, if the suspension is uniformly heated such that the temperature of the suspension reaches a point at which the smaller and less massive particles remain suspended through a heat driven increase in Brownian forces while the larger and more massive particles continue to settle then a portion of the suspension will contain primarily the smaller and less massive particles after a certain period of time. This portion can be physically removed from the suspension or segregated and the differently massed particles will have been separated to some extent. The process can be repeated with the remaining portion of the suspension that still contains some quantity the larger and more massive particle. In this case, additional liquid may be added to the remaining suspension so that the volume equals that of the original suspension, and the particles can be redistributed by agitation. Multiple iterations can be carried out until a complete, nearly complete or satisfactory separation is achieved.

It should be noted that the viscosity of a selected liquid is in general a function of temperature, and that the nanoparticle separation according to the general example described above will be influenced by the rate of change of the viscosity of the liquid with respect to temperature. A separation could also be controlled by otherwise adjusting the viscosity of the liquid. For example, the viscosity of a liquid can be controlled by pressurizing or de-pressurizing the liquid. Viscosity can be controlled by mixing two miscible pure liquids of different, typically greater and lesser viscosities to achieve a desired viscosity. A liquid with a sufficiently low viscosity added to a mixture can increase the sedimentation velocity of larger nanoparticles with respect to smaller nanoparticles in a suspension. Therefore, separation will occur over time when the suspension is under the influence of a force, for example gravity.

Nanoparticle interaction potential can also be modified for different particles through changes in nanoparticle concentration, surface modifications which cause electrostatic stabilization or destabilization, and/or surface modifications that change the van der Waals forces between particles. Surface modifications can be made to particles of different compositions by selectively targeting one nanoparticle with a surface modifier that will react to the targeted nanoparticle with high specificity. Changing the interaction potential of a nanoparticle can change the colloidal stability of the targeted nanoparticles, either making them more stable to resist settling or making the particles more prone to conglomeration so that they settle at a faster rate. Surface modifications may be permanent, or may be reversible or temporary.

In addition, the surface geometry or effective radius of a nanoparticle can be modified through selective surface modifications or through selective surface coatings. In a suspension containing two or more types of nanoparticles, each with a unique composition, one or more of the types of nanoparticles can be selectively modified while in the suspension. Changing the surface geometry or the effective radius of a targeted variety of nanoparticle will alter the diffusivity of the modified nanoparticles, and therefore, will change the settling rate of the particle in a suspension under the influence of a force.

Surface modifications which result in changes in the interaction potential or surface geometry/effective radius of a nanoparticle can also be useful when attempting to separate nanoparticles of approximately the same size and mass but of different compositions so that surfaces can be selectively targeted. Such a case can occur for composite core shell particles where one particle has a denser core but less dense shell than the second particle. The shells are of different compositions, for example, the particles could be of different oxides, and therefore, the particle surfaces can be selectively modified to improve the separation efficiency.

Thus, the methods disclosed herein can be applied to nanoparticles of any structure and/or composition and mixtures of nanoparticles with different structures and/or compositions.

The disclosed methods also may be applied to nanoparticle mixtures that result from non-uniform synthesis of nanoparticles, for example syntheses that result in poly-disperse nanoparticles or mixtures of aggregated and un-aggregated particles. The methods may also be applied to nanoparticle mixtures created by mixing two or more different types of uniform nanoparticles together.

The disclosed separation techniques may be applied to suspensions in any pure liquid, suspensions in combinations of two or more pure liquids, or suspensions in combinations or solutions containing solutes to alter the physical properties, for example the viscosity, of the solution. It may be advantageous in certain instances to use a suspension liquid that does not contaminate the suspended particles. For example, the disclosed techniques may be implemented in water as described below, which typically will not contaminate a particle.

The disclosed methods may be applied to a liquid in any thermodynamic state. For example the liquid may be in thermodynamic equilibrium or quasi-equilibrium. Alternatively, the liquid may not be in thermodynamic equilibrium or quasi-equilibrium. The liquid can be at any temperature. The temperature of liquid during the separation process may be uniform and static, uniform and dynamic, or the liquid may contain temperature gradients that that are static or dynamic.

Since particles such as SERS nanotags are robust, extreme temperatures that would destroy cells or organic molecules may be employed during separation steps.

The disclosed methods include any method of modifying the viscosity of a selected suspension liquid including but not limited to changing the suspension liquid temperature; pressurizing or de-pressurizing the suspension liquid or mixing a suspension liquid of two components each having a different viscosity.

The disclosed methods include any method of applying or causing surface modification to a nanoparticle.

The methods may be implemented in any vessel which may contain a liquid and nanoparticle mixture. The vessel may be sealed or open to the atmosphere, pressurized with any gas, contain ports at any location for the addition or removal of material, or employ a mechanism that creates or fosters laminar or turbulent flow within the liquid and nanoparticle mixture at any point during, before or after the separation process. Any desired transfer of heat to or from the liquid within vessel may take place in any way.

The disclosed methods include any method of removing the liquid during or after the nanoparticle separation process.

The methods apply to any method of generating or utilizing a force, including but not limited to the use of gravity, a device that produces a centrifugal force, or through the use of an electromagnetic force or other physical force upon nanoparticles that are subject to the selected force.

EXAMPLES

The following examples are provided for illustrative purposes only and are not intended to limit the scope of the invention.

Example 1

An example of particle separation as described above, while in progress, is shown in FIG. 1. The nanoparticles used in this example are a combination of spherical silica particles, silica coated spherical gold particles, and silica coated aggregated spherical gold particles. The longest dimension of most particles lies between 50 nm and 500 nm. The nanoparticles started out uniformly distributed with liquid water in a sealed vessel. The suspension was heated above room temperature for 24 hours, and the particles of different sizes, compositions and aggregation levels are observed to settle at different rates. The shaded layers in the suspension, as illustrated in FIG. 1 indicate where different particles are located in the suspension. The top layer 100 contains only silica particles. The layer second from the top 102 contains silica particles and silica coated gold particles. The third layer from the top 104 contains silica particles; silica coated gold particles, and moderately aggregated (2-3 gold particles per aggregate) silica coated gold particles. The bottom layer 106 contains silica particles, silica coated gold particles, moderately aggregated silica coated gold particles, and heavily aggregated silica coated gold particles. The observed level of separation does not take place at room temperature. The character of the separation at an elevated temperature is due to heat induced increase in diffusivity of the smaller particles and a heat induced decrease in the viscosity of the water.

Figure 2A:
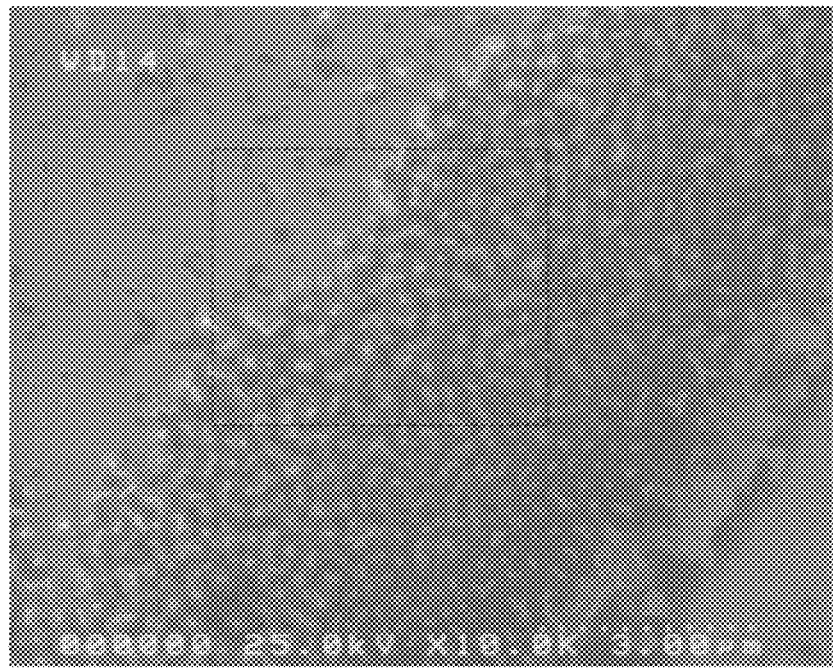
FIG. 2a is an SEM image of a mixture of nanoparticle types prior to separation.
Figure 2B:
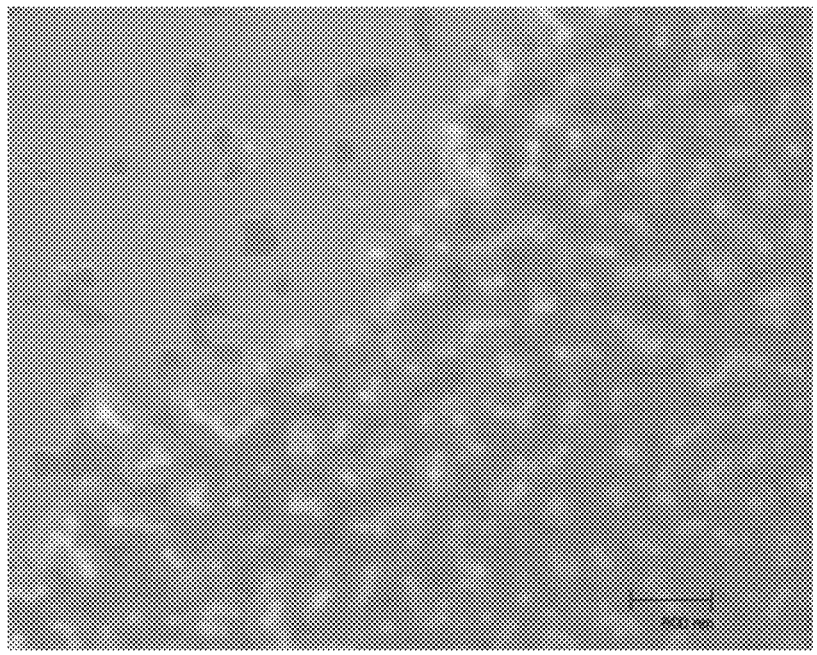
FIG. 2b is an enlarged view of the portion of FIG. 2a enclosed in the dashed box.
Figure 3A:
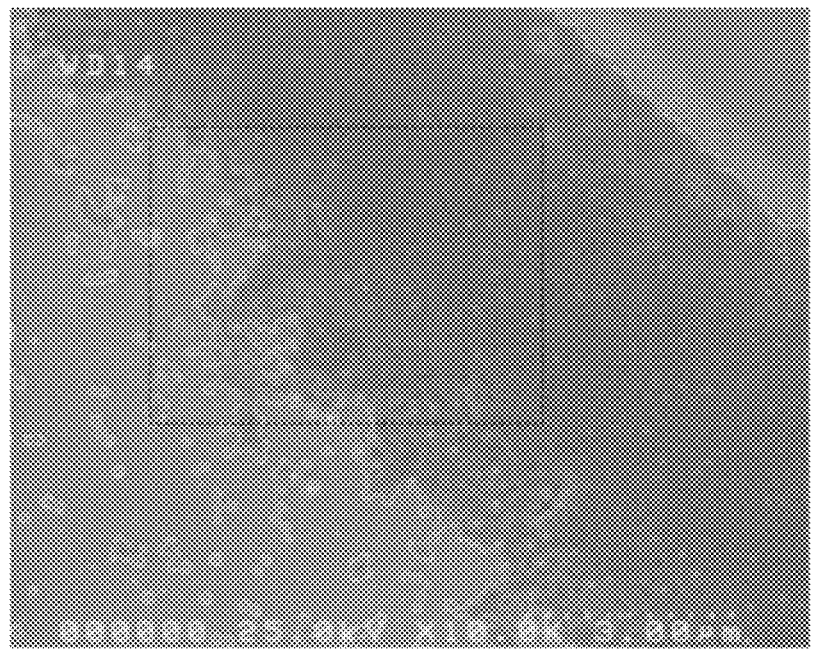
FIG. 3a is an SEM image of a portion of the mixture of nanoparticle types of FIG. 2a removed after a first separation step.
Figure 3B:
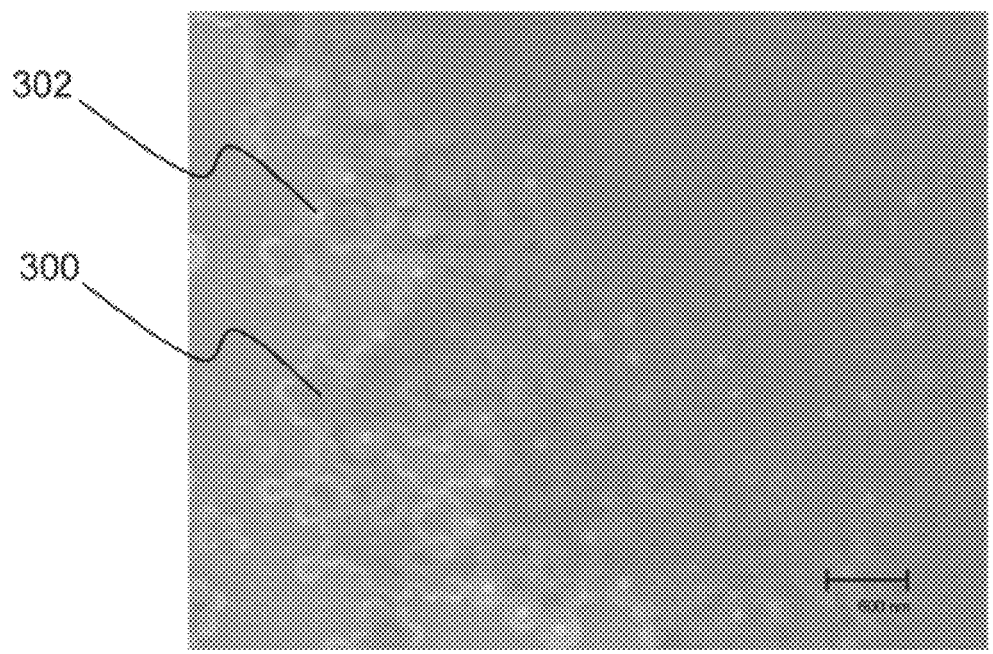
FIG. 3b is an enlarged view of the portion of FIG. 3a enclosed in a dashed box.

Iterations of the described separation at elevated temperature in water were carried out for a similar mixture of particles. FIGS. 2a and 2b are an SEM image of the mixture of particles before separation has taken place. FIG. 2b is an enlarged view of the area contained within the box shown on FIG. 2a. FIGS. 3a, 3b and FIGS. 4a and 4b show particles taken from the first (upper) layer 100 and second layer 102 respectively, formed after the first separation. These layers were removed from the suspension and water was added to the suspension to offset the loss in volume.

Figure 4A:
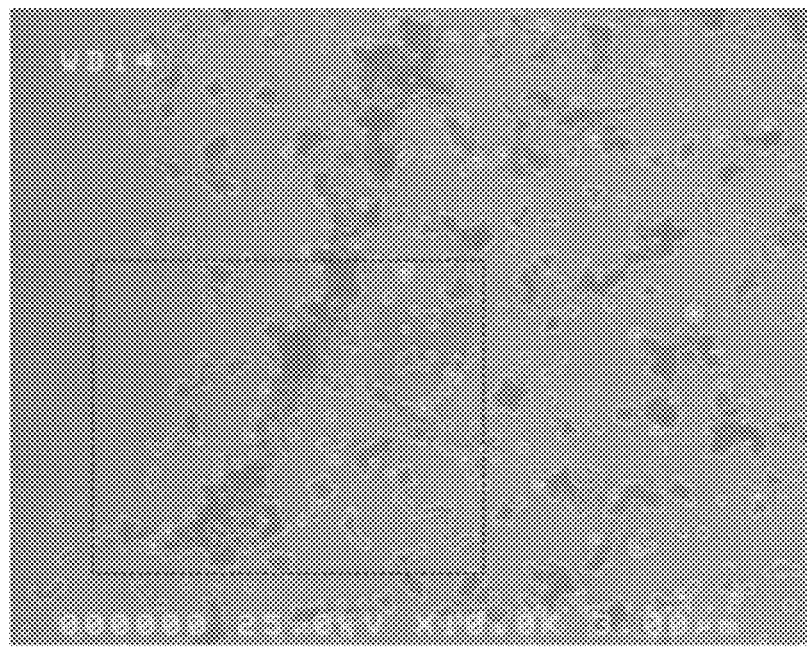
FIG. 4a is an SEM image of another portion of the mixture of nanoparticle types of FIG. 2a removed after a first separation step.
Figure 4B:
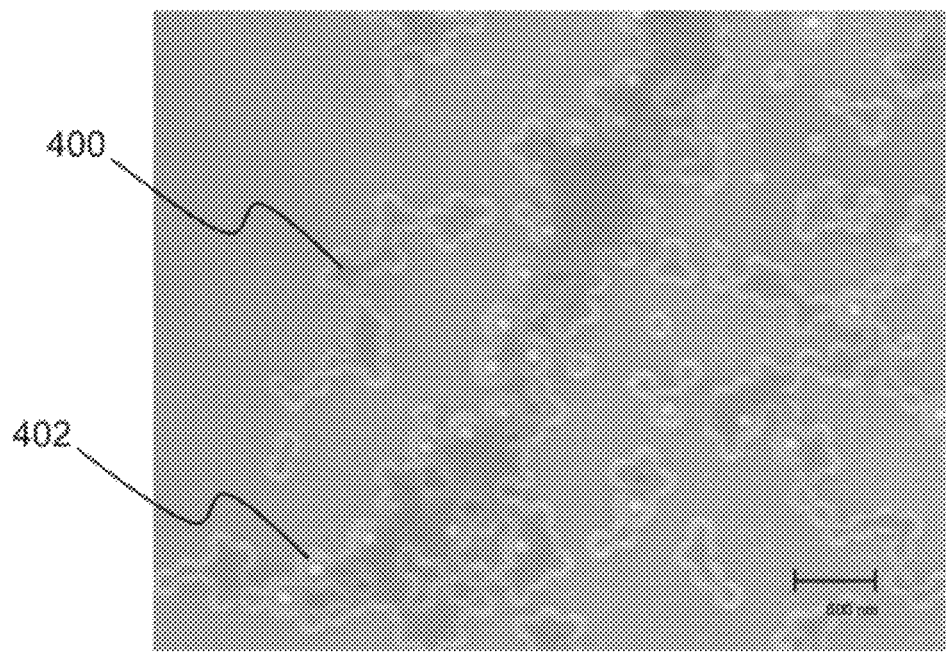
FIG. 4b is an enlarged view of the portion of FIG. 4a enclosed in a dashed box.
Figure 5A:
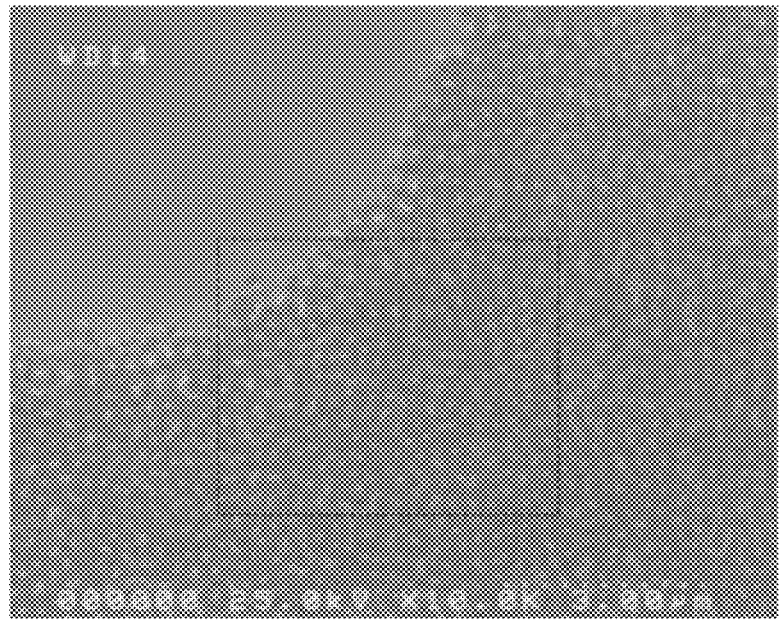
FIG. 5a is an SEM image of a portion of the mixture of nanoparticle types of FIG. 2a removed after a second separation step.
Figure 5B:
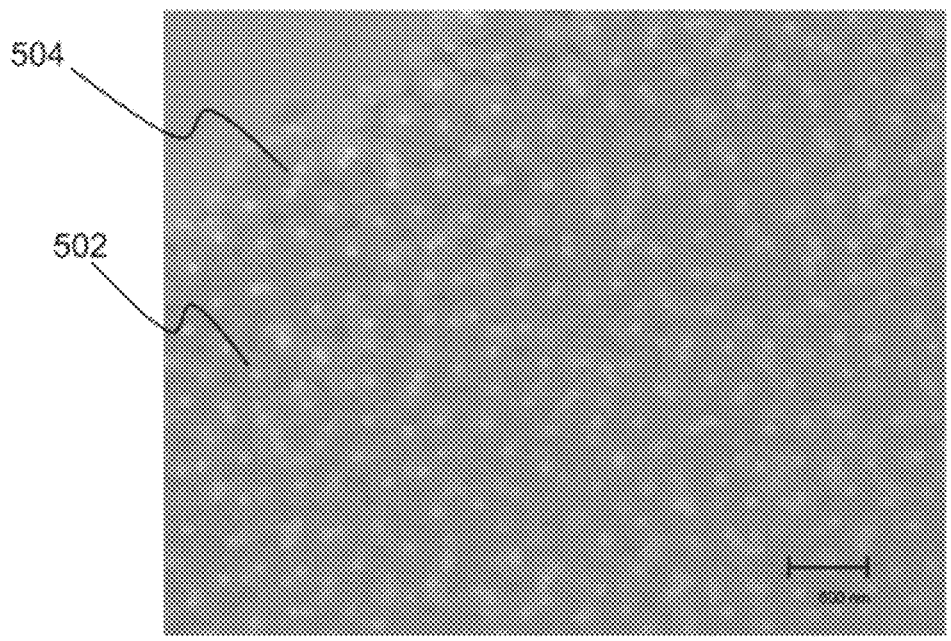
FIG. 5b is an enlarged view of the portion of FIG. 5a enclosed in a dashed box.
Figure 6A:
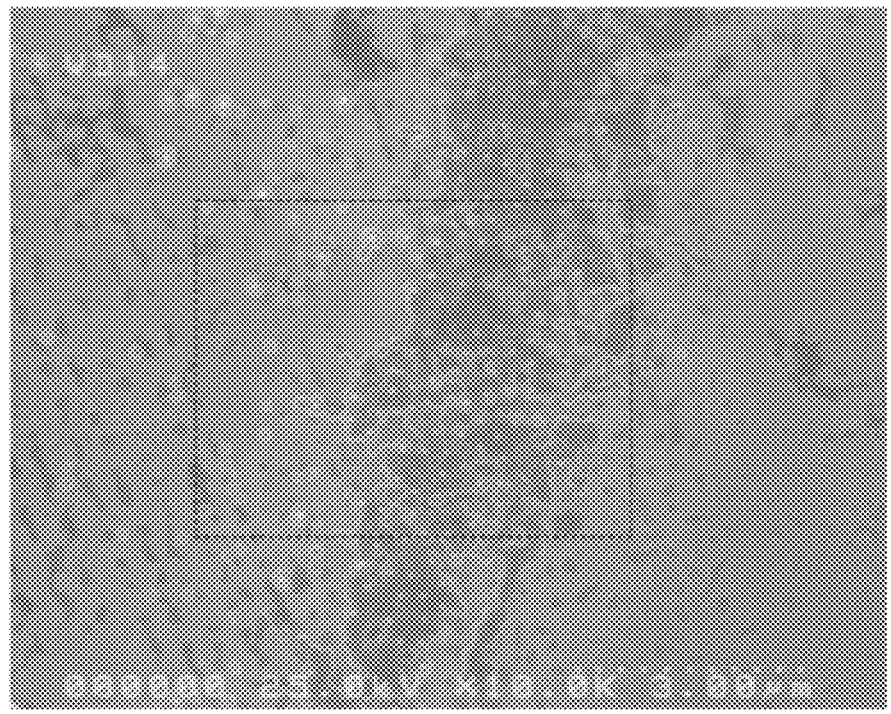
FIG. 6a is an SEM image of a portion of the mixture of nanoparticle types of FIG. 2a removed after a third separation step.
Figure 6B:
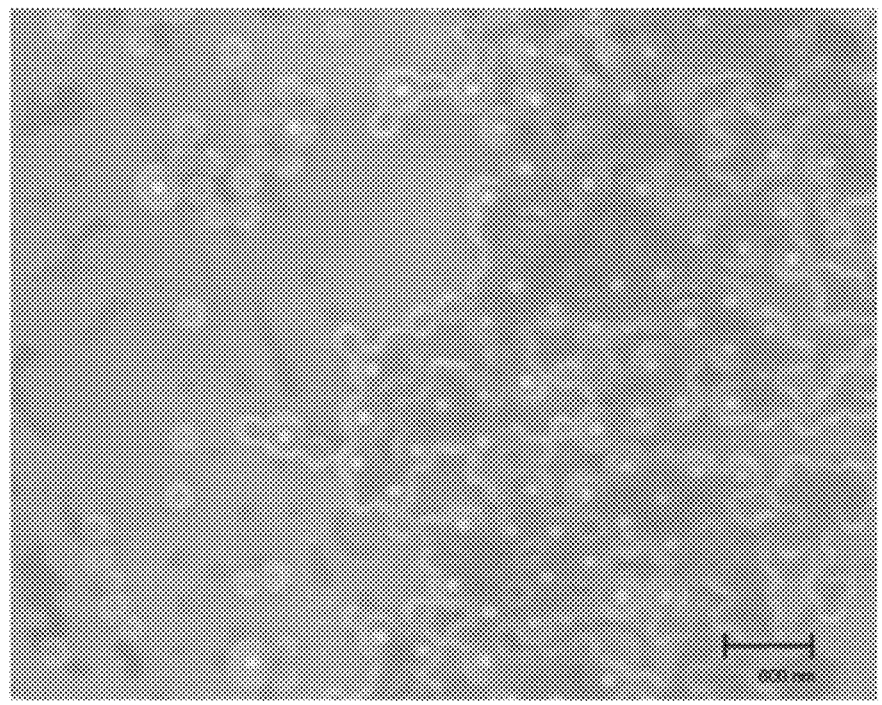
FIG. 6b is an enlarged view of the portion of FIG. 6a enclosed in a dashed box.
Figure 7A:
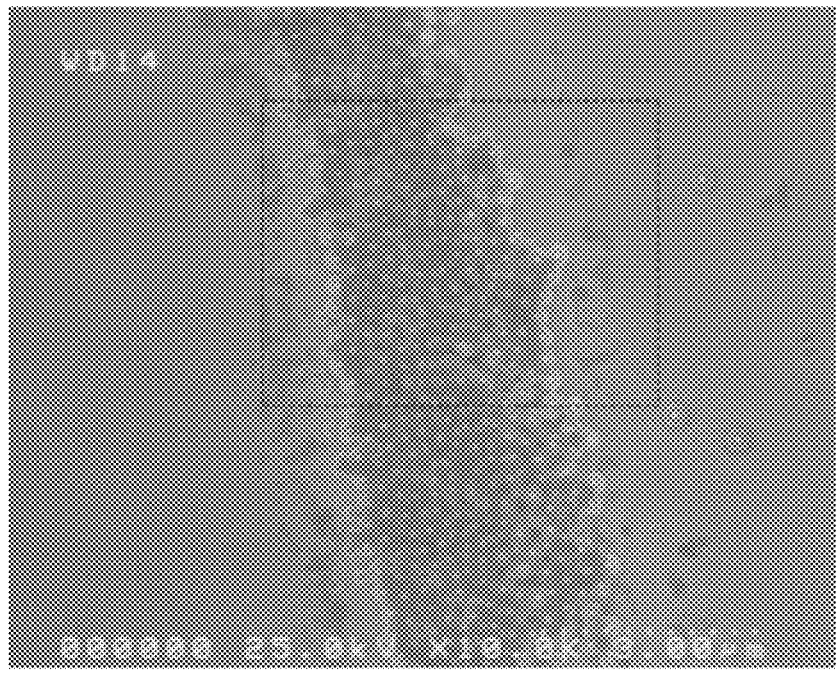
FIG. 7a is an SEM image of a portion of the mixture of nanoparticle types of FIG. 2a removed after a fourth separation step.
Figure 7B:
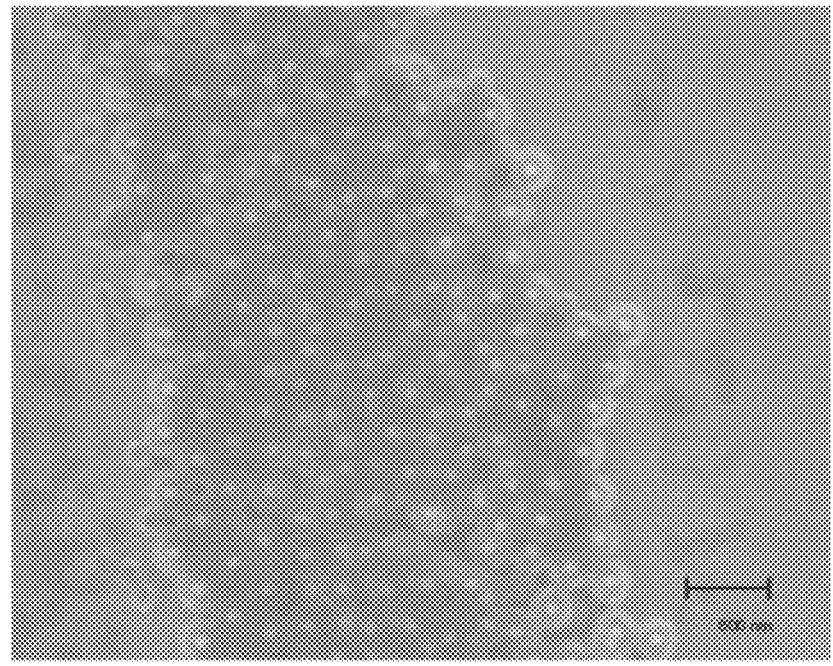
FIG. 7b is an enlarged view of the portion of FIG. 7a enclosed in a dashed box.
Figure 8A:
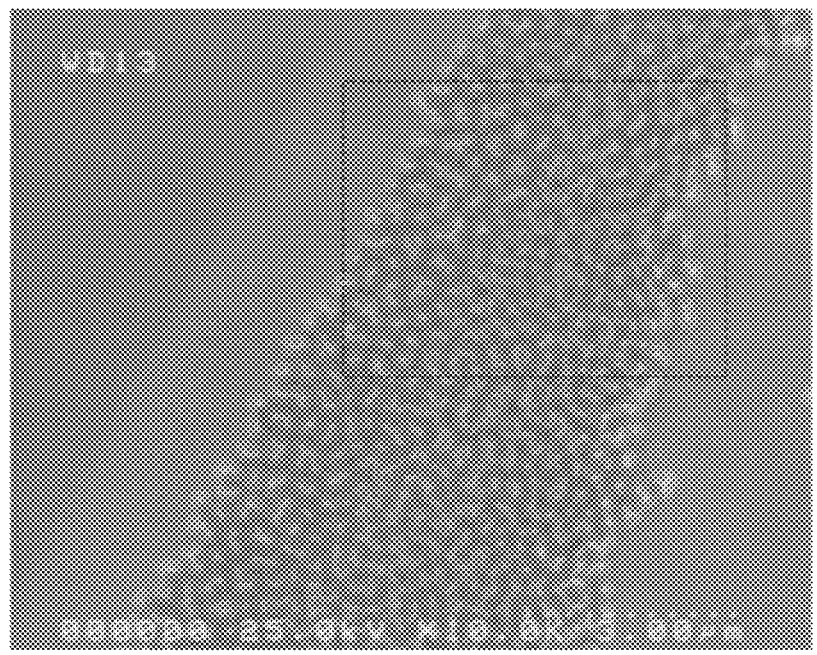
Figure 8B:
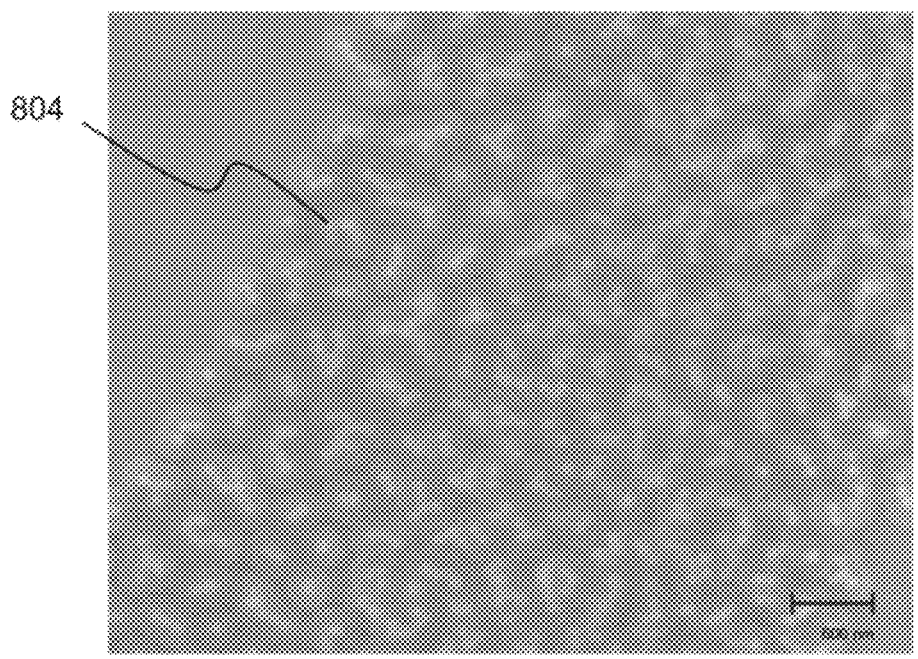
FIG. 8b is an enlarged view of the portion of FIG. 8a enclosed in a dashed box.

FIGS. 5a, 5b show the particles in the first (upper) layer removed after a second separation. FIGS. 6a, 6b and FIGS. 7a, 7b show particles samples from the first (upper) layers of the sample after third and fourth separations, respectively. FIGS. 8a, 8b show the remaining material after a fourth separation process. I may be noted from FIGS. 2-8 that the each subsequently removed layer shows a reduced amount of silica particles and silica coated gold particles. In particular it may be noted from FIG. 3b which is a sample from the first (upper) layer of the first separation that the sample is predominately silica particles 300 with relatively few silica coated gold particles 302. Aggregated coated gold particles are substantially absent from this layer. FIG. 4b, sampled from the second layer after one separation step shows relatively fewer silica particles 400 and relatively more coated gold particles 402 than the first for example the silica particle in the remaining suspension.

The proportion of aggregated particles to other particles is show to be increased after each separation. In particular, FIG. 5b which shows the particles in an upper layer after a second agitation and second heat induced separation step. FIG. 5b shows a mixture of coated gold particles 502 and aggregated coated gold particles 504 with very few remaining silica particles. FIG. 8a shows a sample taken from the lower layer after multiple separation steps and clearly shows a predominance of aggregated gold particles 804.

Figure 9:
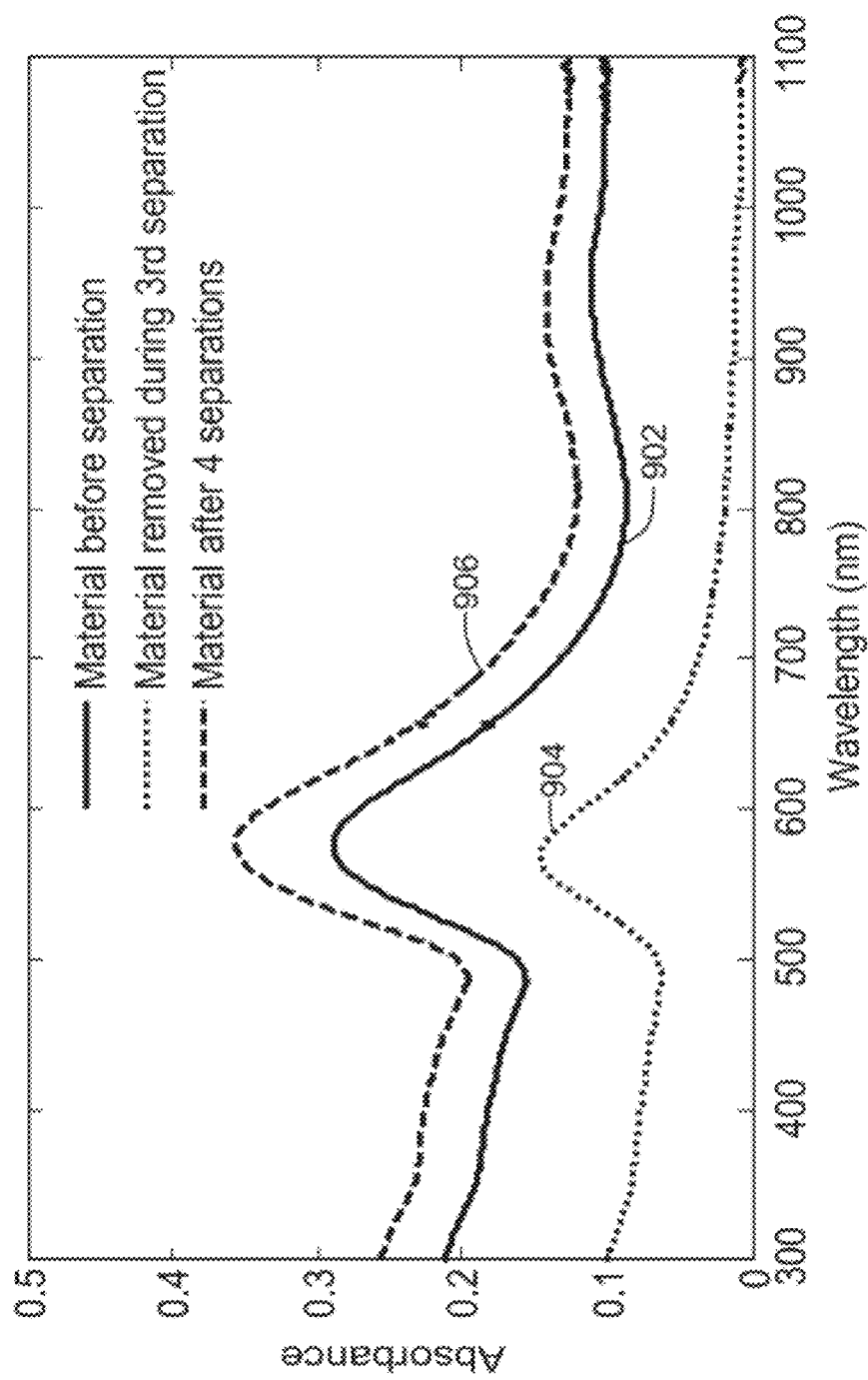
FIG. 9 is a graph showing optical extinction spectra of the particle mixture of FIG. 2a, before and after separation has taken place.
Figure 10:
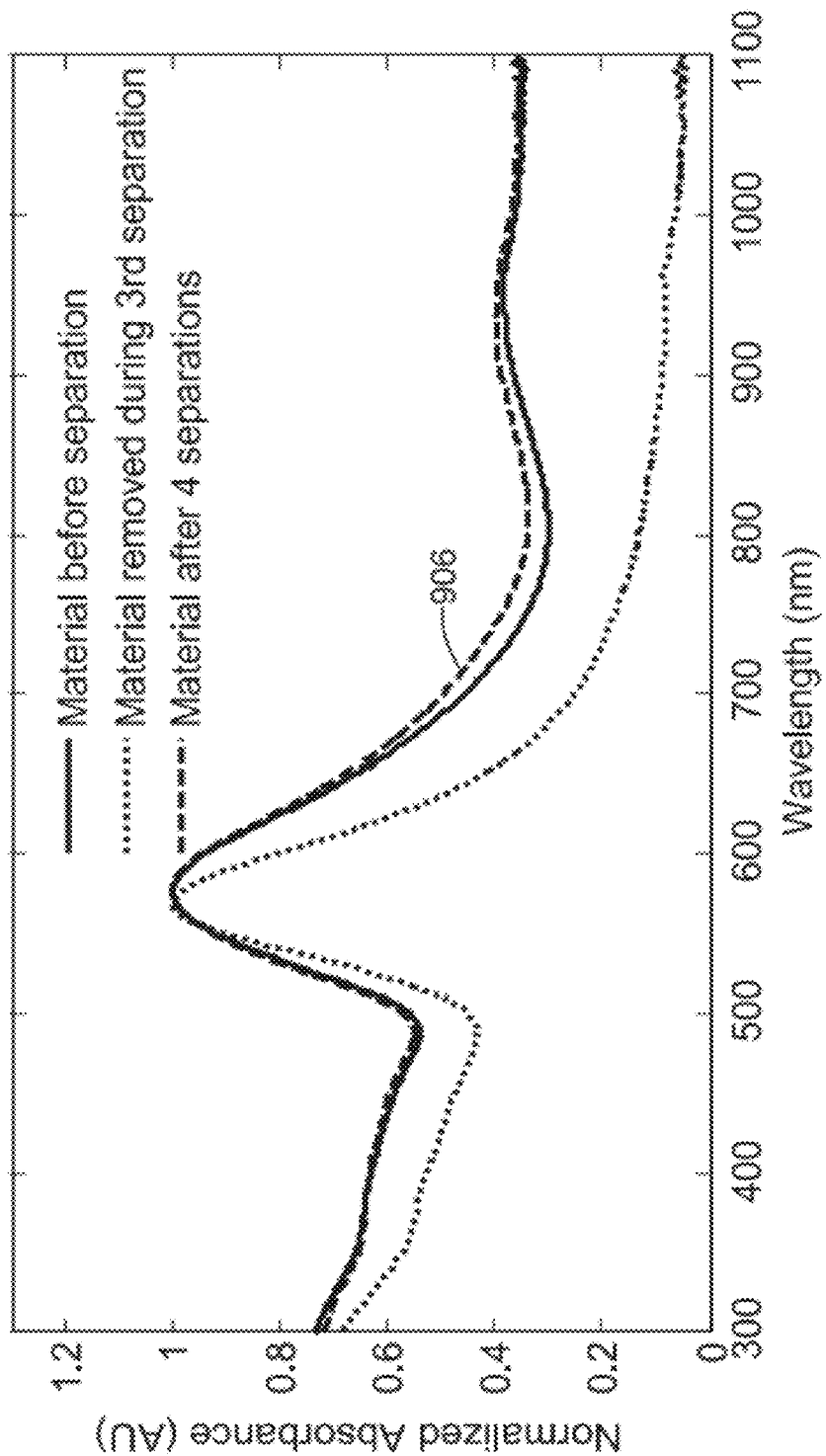
FIG. 10 is a graph showing the optical extinction spectra of FIG. 9 normalized by maximum signal.

The spectra of FIG. 9 graphically illustrate the optical extinction properties for the particle mixture of Example 1 at different stages of a multiple step heated separation process as described above. Trace 902 shows the optical extinction properties of a suspension before a separation has taken place. Trace 904 shows the optical extinction properties of material removed from the upper layer during a third separation. Trace 906 shows the optical extinction properties of the remaining material after 4 separations. The lack of a peak in the absorbance spectra at wavelengths greater than 800 nm for the material removed during the third separation (Trace 904) indicates that the removed material did not contain aggregated particles. FIG. 10 shows the same optical extinction spectra shown in FIG. 9 but with each spectrum normalized by its maximum signal. The normalization shows that the material remaining after four separations (Trace 906) has a relatively greater peak in the absorbance at wavelengths longer than 800 nm than the material before separation has taken place. This further confirms that the heated separation techniques have resulted in the increase of aggregated particle concentration relative to other particles.

Example 2

Example 2 involves the heat driven separation of spherical silica coated gold nanoparticles from silica coated aggregated spherical gold particles. The Example 2 particles were specifically prepared to have a variety of aggregation states. In particular, the material for Example 2 was prepared to contain a very large population of spherical coated gold particles (~70%) relative to silica coated aggregated spherical gold particles (~30%).

The nanoparticles were initially uniformly distributed in water in a sealed container, observing procedures similar to those described above in Example 1. The suspension was treated to five sequential separation iterations at temperatures of 80° C., 75° C., 70° C., 65° C., and 60° C. respectively. The separation time varied with temperature and the concentration of the sample. In particular, the separation times observed for a volume of 1.75 mL of material at a specific concentration were as follows:
Cycle 1=2 days
Cycle 2=1.5 days
Cycle 3, 4, and 5=<1 day, each The particles were observed to settle at different rates and shaded layers forming in the suspension in a manner similar to that illustrated in FIG. 1 were similarly observed for this sample.

Figure 11:
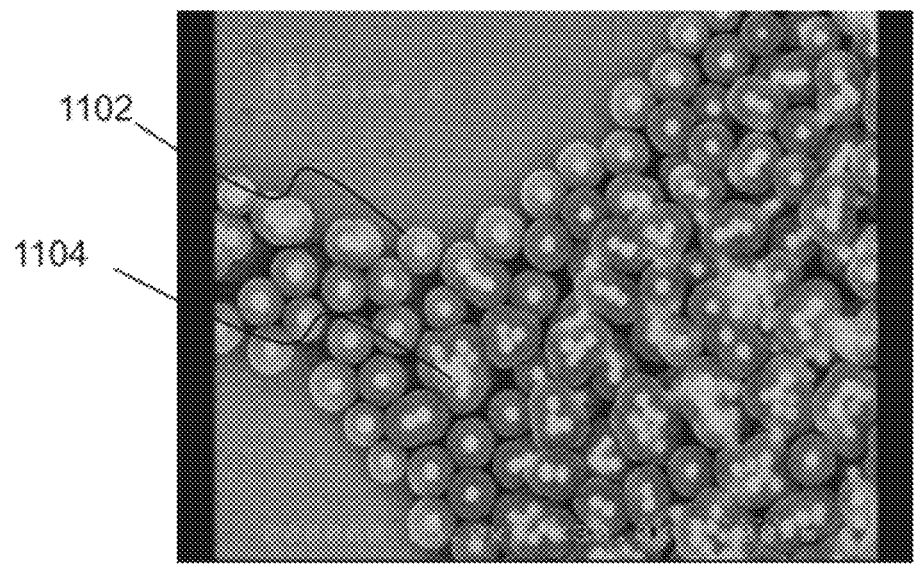
FIG. 11 is an SEM image of a mixture of nanoparticle types prior to separation.
Figure 12:
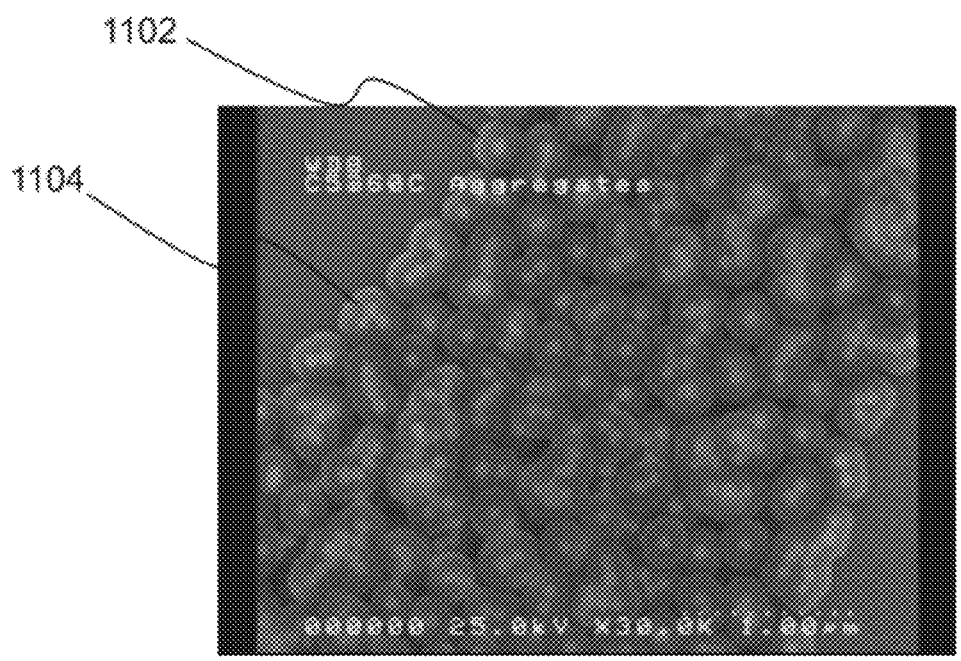
FIG. 12 is an SEM image of a portion of the mixture of nanoparticle types of FIG. 11 remaining after five separation steps.

FIG. 11 is a SEM image of the Example 2 mixture of particles before any separation steps have taken place. FIG. 12 is a SEM image of the Example 2 mixture of particles remaining after five steps of separation had been performed as described above. As clearly shown by comparing these two SEM images, the proportion of aggregated particles 1104 to non-aggregated particles 1102 is significantly increased after five separations.

Figure 13:
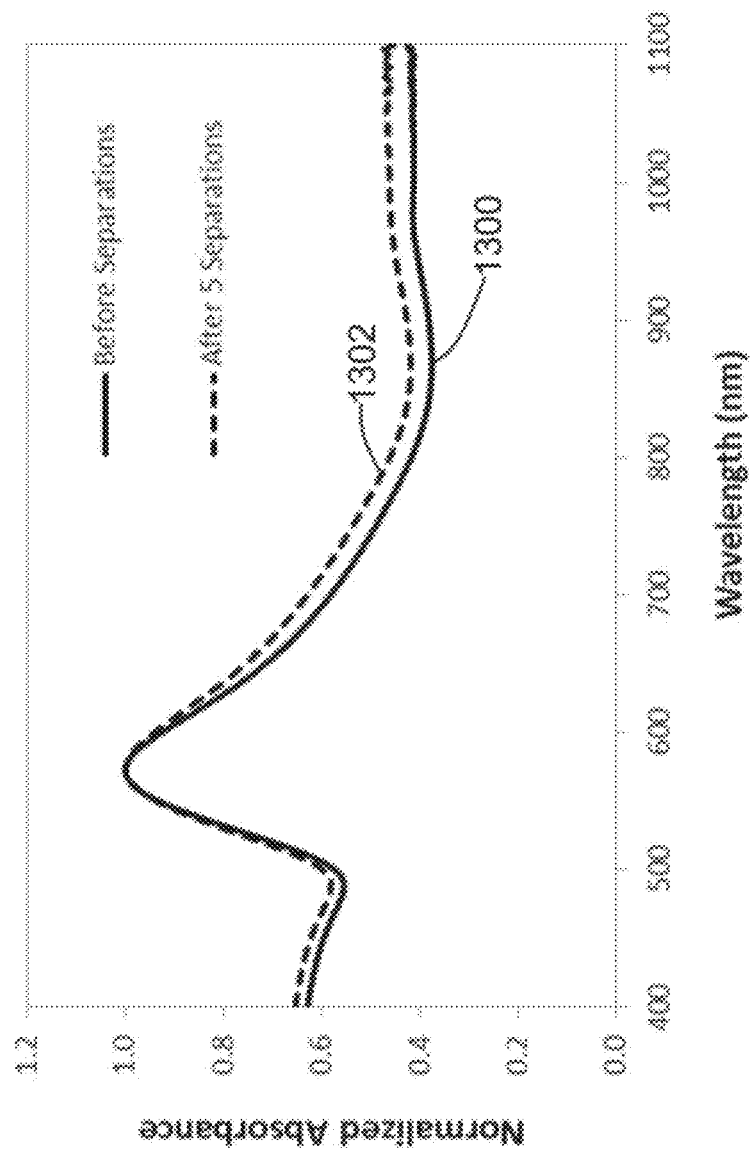
FIG. 13 is a graph showing the normalized optical extinction spectra of the FIG. 11 and FIG. 12 particle mixtures.

Normalized optical extinction spectra for the particle mixture before any separations had taken place (Trace 1300) and after five separations had been performed as described above (Trace 1302) are presented in FIG. 13. As observed in Example 1, the material remaining after five separations has a relatively greater peak in the absorbance spectrum for wavelengths longer than 800 nm. This observation confirms that the aggregated particle concentration has increased after the separation process as shown in the SEM image of FIG. 12.

Example 3

Example 3 involves spherical silica coated gold particles and silica coated aggregated spherical gold particles identical to those used in Example 2 but suspended in a water/glycerol mixture. This example illustrates that modification of the viscosity of the selected suspension liquid can lead to increased separation efficiency. In Example 3, the selected nanoparticles were uniformly distributed in 60% by volume glycerol to water mixture in a sealed container. The viscosity of the described glycerol/water mixture is higher than the viscosity of water alone. The suspension was treated to four separation iterations each at a temperature of 60° C. for the following observed separation times:
Cycle 1=3 days
Cycle 2=2 days
Cycle 3, 4=1.5 days, each The particles were observed to settle at different rates and the container exhibited shaded layers similar to those illustrated in FIG. 1. It was noted that the total separation time was longer in this example when compared to Example 2, but fewer separation iterations were required to achieve the same level of separation.

Figure 14:
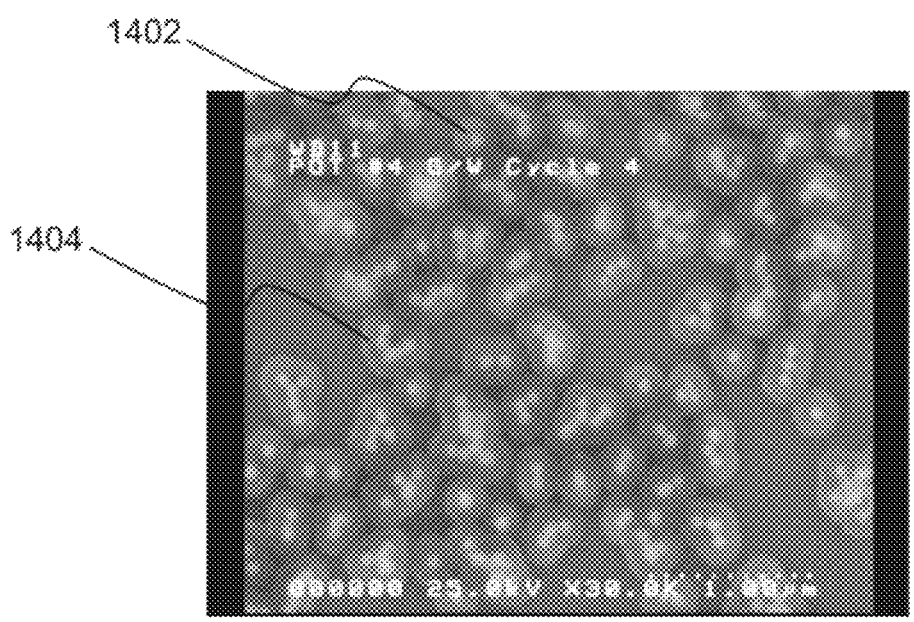
FIG. 14 is an SEM image of a portion of a mixture of nanoparticle types remaining after four separation steps in a suspension liquid mixture.
Figure 15:
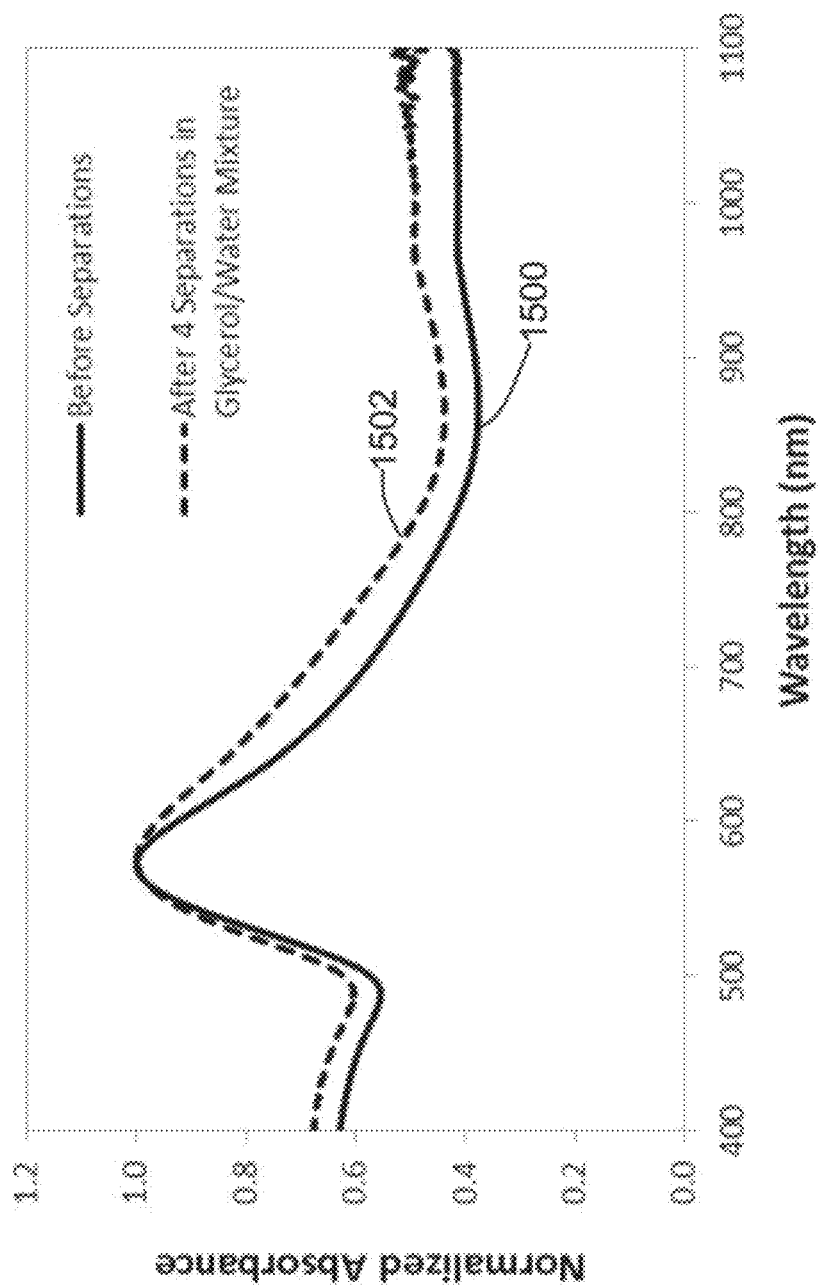
FIG. 15 is a graph showing the normalized optical extinction spectra of the FIG. 14 particle mixture before and after separation.

After the separation steps noted above were completed, the particles were centrifuged and re-suspended in water prior to data collection. FIG. 11 is a SEM image of the Example 3 mixture of particles before any separation steps have taken place. FIG. 14 is a SEM image of the Example 3 mixture of particles remaining after four steps of separation at elevated temperature in the water and glycerin suspension liquid had been performed as described above. The proportion of aggregated particles 1404 to non-aggregated particles 1402 was observed to be increased after each separation and the population of single particles was significantly decreased. Normalized optical extinction spectra for the particle mixture before any separations had taken place (Trace 1500) and after four separations had been performed as described above (Trace 1502) are presented in FIG. 15. As observed in Example 2, the material remaining after four separations has a relatively greater peak in the absorbance spectrum for wavelengths longer than 800 nm. This observation confirms that the aggregated particle concentration has increased after the separation process as shown in the SEM image of FIG. 14.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the disclosure has been particularly shown and described with reference to a number of embodiments, it would be understood by those skilled in the art that changes in the form and details may be made to the various embodiments disclosed herein without departing from the spirit and scope of the disclosure and that the various embodiments disclosed herein are not intended to act as limitations on the scope of the claims. All references cited herein are incorporated in their entirety by reference.

What is claimed is:

1. A method of separating a mixture of more than one type of nanoparticle according to nanoparticle type, the method comprising:
suspending the mixture of more than one type of nanoparticle in a suspension liquid having a viscosity;
modifying the viscosity of the suspension liquid by adding a second liquid having a different viscosity to the suspension liquid to create a modified suspension liquid;
applying a force to the mixture of more than one type of nanoparticle suspended in the modified suspension liquid, causing physical separation of the nanoparticles by type; and
removing a selected portion of the separated nanoparticles from the modified suspension liquid.

2. The method of separating a mixture of more than one type of nanoparticle according to nanoparticle type of claim 1 further comprising modifying the temperature of the suspension liquid.

3. The method of separating a mixture of more than one type of nanoparticle according to nanoparticle type of claim 1 further comprising modifying the pressurization of the suspension liquid.

4. The method of separating a mixture of more than one type of nanoparticle according to nanoparticle type of claim 3 wherein the suspension liquid is water.

5. The method of separating a mixture of more than one type of nanoparticle according to nanoparticle type of claim 1 wherein the suspension liquid is selected to not contaminate one or more of the nanoparticle types.

6. The method of separating a mixture of more than one type of nanoparticle according to nanoparticle type of claim 1 further comprising utilizing a first portion of the separated nanoparticles as a taggant and recycling a second portion of the separated nanoparticles.

* * * * *